(12) United States Patent
Walther et al.

(10) Patent No.: US 8,473,215 B2
(45) Date of Patent: Jun. 25, 2013

(54) METHOD FOR CLUSTERING DATA ITEMS THROUGH DISTANCE-MERGING AND DENSITY-MERGING TECHNIQUES

(75) Inventors: Guenther Walther, Mountain View, CA (US); Ilana Belitskaya-Levy, New York, NY (US); Jinhui Pan, Mountain View, CA (US); Leonore A. Herzenberg, Stanford, CA (US); Wayne Moore, San Francisco, CA (US); David Parks, San Francisco, CA (US)

(73) Assignee: Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/832,992

(22) Filed: Apr. 26, 2004

(65) Prior Publication Data

US 2011/0029519 A1 Feb. 3, 2011

Related U.S. Application Data

(60) Provisional application No. 60/465,703, filed on Apr. 25, 2003.

(51) Int. Cl.
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 5,414,797 A | 5/1995 | Vassiliadis et al. | |
| 5,796,986 A | 8/1998 | Fuller | |
| 6,178,382 B1 * | 1/2001 | Roederer et al. | 702/21 |
| 6,304,868 B1 | 10/2001 | Vingron et al. | |
| 6,345,265 B1 | 2/2002 | Thiesson et al. | |
| 6,460,035 B1 | 10/2002 | Siegwart | |
| 6,466,946 B1 | 10/2002 | Mishra et al. | |
| 6,490,582 B1 | 12/2002 | Fayyad et al. | |
| 6,496,834 B1 | 12/2002 | Cereghini et al. | |
| 6,556,983 B1 * | 4/2003 | Altschuler et al. | 706/55 |
| 6,763,148 B1 * | 7/2004 | Sternberg et al. | 382/293 |
| 7,227,985 B2 * | 6/2007 | Ikeda et al. | 382/159 |

OTHER PUBLICATIONS

Kowalewski et al. (Pattern Recognition, 1995, Vo. 28, No. 12, p. 1973-1984).*
Casey et al. (Physiol. Genomics, 2002, 8, p. 115-122; First published Dec. 18, 2001).*
http://mathworld.wolfram.com/Gradient.html, Copyright 1999, p. 1-2.*
Patane et al. (IEEE Transactions on Neural Networks, 2002, 13, p. 1285-1298).*
Karypis et al., Computer, Aug. 1999, vol. 32, No. 8, p. 68-75.*
Boddy et al., Cytometry, 2001, vol. 44, p. 195-209.*
Essam et al., Review of Modern Physics, 1970, vol. 42, No. 2, p. 272-288.*
Wu et al. (IEEE Transactions on Pattern Analysis and Machine Intelligence; 1993; vol. 15, No. 11; p. 1101-1113).*
Murtagh (Clustering in Massive Data Sets; Jul. 10, 2000; p. 1-32).*
Murphy (Cytometry, 1985, 6:302-309).*
Fukunaga et al. (1975) "The estimation of the gradient of a density function, with applications in pattern recognition." *IEEE Trans. Info. Thy.* IT-21, 32-40.
Kittler (1976) "A locally sensitive method for cluster analysis." *Pattern Recognition* 8, 23-33.
Koontz et al. (1976) "A graph-theoretic approach to nonparametric cluster analysis." *IEEE Trans. Comput.* C-25, 936-943.
Wand (1994) "Fast computation of multivariate kernel estimators." *Journal of Computational and Graphical Statistics* 3, 433-445.

* cited by examiner

*Primary Examiner* — Pablo S Whaley
(74) *Attorney, Agent, or Firm* — Quine Intellectual Property Law Group, P.C.; Stephen J. LeBlanc

(57) ABSTRACT

A method and/or system for analyzing data using population clustering through density based merging.

7 Claims, 4 Drawing Sheets

| | ForSc | OrthSc | <Fluor> | <PhyEry> | <Cy5PE> | <TexRed> | <AlPhCy> | <Cy7APC> | <Cy7PE> | <CasBlu> | <Cy55PE> | <Cy55AP> |
|---|---|---|---|---|---|---|---|---|---|---|---|---|
| 1 | 352 | 6.65 | 0.26 | 16.6 | 0.56 | 0.79 | 8.71 | 0.82 | 17.6 | 1.45 | 7.92 | 0.1 |
| 2 | 228 | 7.06 | 0.31 | 14.7 | 0.1 | 6.57 | 6.88 | 0.97 | 24.6 | 1.38 | 27.8 | 1.32 |
| 3 | 238 | 6.76 | 0.56 | 21.2 | 1.05 | 0.33 | 16.7 | 0.1 | 0.1 | 1.51 | 9.08 | 0.22 |
| 4 | 240 | 9.86 | 0.1 | 6.32 | 0.1 | 26.3 | 5.28 | 0.1 | 849 | 1.67 | 19.6 | 0.1 |
| 5 | 234 | 6.13 | 0.39 | 14.1 | 1.07 | 7.85 | 8.57 | 0.62 | 0.1 | 2.01 | 20.2 | 1.86 |
| 6 | 395 | 6.82 | 0.13 | 14.2 | 0.63 | 7.46 | 0.1 | 1.99 | 2.43 | 1.85 | 19.5 | 0.1 |
| 7 | 237 | 6.95 | 0.36 | 10.1 | 0.63 | 0.12 | 3.07 | 1.73 | 31.7 | 0.42 | 12.7 | 0.1 |
| 8 | 337 | 6.21 | 0.2 | 12.9 | 0.27 | 7.09 | 2.28 | 0.1 | 80.3 | 1.45 | 16.7 | 0.4 |
| 9 | 254 | 11 | 0.22 | 17.2 | 1.41 | 12.1 | 7.11 | 1.58 | 24.1 | 1.22 | 12.9 | 0.17 |
| 10 | 326 | 4.88 | 0.58 | 23.8 | 0.44 | 1.96 | 88.7 | 2.49 | 5.5 | 0.32 | 10.5 | 30.5 |
| 11 | 236 | 12.8 | 0.51 | 18.6 | 0.84 | 15.1 | 1.12 | 0.1 | 214 | 1.38 | 28.7 | 2.45 |
| 12 | 311 | 8.93 | 0.63 | 4.62 | 0.37 | 1.52 | 8.49 | 0.62 | 4.85 | 0.39 | 11.3 | 1 |
| 13 | 250 | 10.8 | 0.33 | 19.9 | 0.17 | 4.18 | 4.24 | 1.62 | 75.5 | 1.97 | 15 | 0.1 |
| 14 | 336 | 9.79 | 0.6 | 13.5 | 2.46 | 10.9 | 105 | 1.37 | 0.1 | 1.75 | 21.4 | 5.45 |
| 15 | 280 | 6.6 | 0.8 | 18.6 | 0.37 | 1.86 | 9.03 | 0.66 | 19.4 | 1.89 | 8.14 | 0.79 |
| 16 | 286 | 7.58 | 0.41 | 13.8 | 0.1 | 0.47 | 6.09 | 1.52 | 14.2 | 1.81 | 18 | 0.1 |
| 17 | 262 | 5.75 | 0.44 | 12.8 | 0.1 | 0.56 | 6.74 | 2.23 | 2.93 | 1.85 | 13.7 | 0.41 |
| ... | | | | | | | | | | | | |
| 9510 | 247 | 8.09 | 0.41 | 18.2 | 0.53 | 0.1 | 22.7 | 0.39 | 7.8 | 0.79 | 16.5 | 0.68 |
| 9511 | 432 | 9.37 | 0.71 | 17.4 | 0.45 | 9.14 | 5.18 | 1.46 | 51.5 | 1.08 | 13.9 | 0.89 |
| 9512 | 448 | 10.3 | 0.52 | 18.5 | 0.1 | 8.09 | 4.78 | 1.07 | 7.92 | 1.45 | 32.5 | 0.5 |
| 9513 | 214 | 7.74 | 0.34 | 15.9 | 1.16 | 6.8 | 1.28 | 1.19 | 1.68 | 1.75 | 14.6 | 0.9 |
| 9514 | 314 | 10.1 | 0.51 | 12.4 | 0.17 | 4.02 | 0.46 | 2.47 | 85.9 | 1.31 | 25.4 | 0.51 |
| 9515 | 234 | 7.53 | 0.44 | 9.98 | 0.1 | 5.01 | 0.43 | 0.3 | 53.5 | 0.99 | 19.9 | 0.1 |
| 9516 | 213 | 7.21 | 0.48 | 7.41 | 0.21 | 0.69 | 0.12 | 0.42 | 3.38 | 0.66 | 8.55 | 0.43 |
| 9517 | 216 | 8.24 | 0.35 | 8.03 | 0.66 | 5.42 | 7.53 | 0.1 | 83.5 | 1.52 | 20.1 | 2.17 |
| 9518 | 307 | 6.96 | 0.36 | 17.9 | 0.12 | 7.24 | 4.93 | 0.1 | 0.31 | 0.66 | 13.5 | 0.51 |
| 9519 | 214 | 8.22 | 0.41 | 19.4 | 0.12 | 1.6 | 6.73 | 0.1 | 57.9 | 1.93 | 16.4 | 1.95 |
| 9520 | 173 | 5.27 | 0.31 | 18 | 0.1 | 2.5 | 9.18 | 0.91 | 0.69 | 1.61 | 7.55 | 1.19 |
| 9521 | 392 | 9.5 | 0.31 | 18.1 | 0.67 | 2.23 | 7.53 | 1.88 | 0.1 | 2.01 | 12.6 | 0.1 |
| 9522 | 429 | 5.43 | 0.65 | 17.1 | 1.86 | 7.11 | 10.9 | 1.85 | 3.01 | 1.26 | 8.11 | 0.1 |
| 9523 | 308 | 8.85 | 0.64 | 29.3 | 1.96 | 4 | 6.68 | 0.8 | 3.54 | 1.96 | 23.1 | 0.91 |
| 9524 | 296 | 8.59 | 0.56 | 20.4 | 0.44 | 6.11 | 8.09 | 0.67 | 3.79 | 1.54 | 28.6 | 1.19 |
| 9525 | 354 | 9.25 | 0.65 | 16.7 | 0.1 | 12.6 | 0.1 | 0.65 | 102 | 1.88 | 34.4 | 0.1 |
| 9526 | 260 | 7.78 | 0.4 | 21.4 | 0.94 | 2.21 | 7.8 | 0.33 | 0.1 | 1.5 | 16 | 1.35 |
| 9527 | 300 | 7.71 | 0.57 | 36.8 | 1.18 | 1.25 | 121 | 2.38 | 3.84 | 0.79 | 7.57 | 24.9 |
| 9528 | 172 | 7.14 | 0.46 | 11.4 | 0.44 | 0.75 | 8.47 | 0.84 | 5.15 | 1.26 | 15.8 | 0.1 |
| 9529 | 265 | 5.66 | 0.18 | 5.17 | 0.1 | 233 | 1.68 | 0.1 | 0.1 | 0.45 | 9.03 | 4.75 |
| 9530 | 378 | 9.73 | 0.67 | 16 | 0.1 | 12.6 | 2.13 | 0.1 | 278 | 1.6 | 32.5 | 0.46 |
| 9531 | 222 | 7.03 | 0.36 | 16.8 | 0.1 | 17.9 | 6.28 | 0.1 | 6.93 | 1.62 | 23.1 | 1.42 |
| 9532 | 419 | 9.93 | 0.64 | 18.9 | 0.31 | 7.81 | 3.37 | 0.37 | 111 | 1.13 | 23.9 | 0.1 |
| 9533 | 353 | 7 | 0.58 | 13.4 | 0.25 | 20.2 | 0.1 | 0.84 | 0.96 | 1.63 | 15.5 | 0.1 |

*FIG. 1*

METHOD FOR CLUSTERING DATA ITEMS THROUGH DISTANCE-MERGING AND DENSITY-MERGING TECHNIQUES

CROSS REFERENCE TO RELATED APPLICATIONS

This application claims priority from provisional patent application 60/465,703, filed 25 Apr. 2003 and incorporated herein by reference.

This invention was made with Government support under contract HL68522 awarded by the National Institutes of Health. The Government has certain rights in this invention.

COPYRIGHT NOTICE

Pursuant to 37 C.F.R. 1.71(e), applicants note that a portion of this disclosure contains material that is subject to and for which is claimed copyright protection, such as, but not limited to, source code listings, screen shots, user interfaces, or user instructions, or any other aspects of this submission for which copyright protection is or may be available in any jurisdiction. The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

COMPACT DISC PROGRAM LISTING APPENDIX

Attached herewith is a compact disc program listing appendix illustrating example source code illustrating specific implementations of specific embodiments of the invention.

FIELD OF THE INVENTION

The present invention relates to the field of data analysis. More specifically, the invention relates to an information system and/or method for making certain determinations regarding data sets.

In some embodiments, the invention involves a data analysis strategy useful in biologic settings, such as analyzing large populations of biologic samples. In further specific embodiments, the invention involves a data analysis method useful in cell analysis methods, such as FACS. In further specific embodiments, the invention involves a data analysis method useful in analyzing market or other data sets. In further specific embodiments, the invention involves a data analysis method useful in analysis of protein and/or genetic and/or chemical and/or other research and/or industrial data.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

In many different industrial, medical, biological, business, research and/or other settings, it is desirable to make some determinations from data sets. Both the art of data analysis and it applications have developed dramatically in recent years.

However, data analysis is often hindered by the amount of data that must be handled and the questions that can be answered thereby. Thus, various proposals have been made for Probabilistic Data Clustering, such as that discussed in U.S. Pat. No. 6,460,035 and its cited art. These proposals fall short in many applications.

Other References

Fukunaga, K. and Hostetler, L. D. (1975). The estimation of the gradient of a density function, with applications in pattern recognition. *IEEE Trans. Info. Thy.* IT-21, 32-40

Kittler, J. (1976). A locally sensitive method for cluster analysis. *Pattern Recognition* 8, 23-33

Koontz, W. L. G., Narenda, P. M. and Fukunaga, K. (1976). A graph-theoretic approach to nonparametric cluster analysis. *IEEE Trans. Comput.* C-25, 936-943

Wand, M. P. (1994). Fast computation of multivariate kernel estimators. *Journal of Computational and Graphical Statistics* 3, 433-445

SUMMARY

Various methods for analyzing data can be employed in specific embodiments. According to specific embodiments, of the invention is directed to cluster creation and determines one or more useful clusters, groupings, and/or populations to which the data belongs. The invention can be used in several areas including flow cytometry analysis and analysis of marketing data. The invention may also be used with in any field in which it is found helpful to cluster and/or group data.

Various embodiments of the present invention provide methods and/or systems for analysis that can be implemented on a general purpose or special purpose information handling system using a suitable programming language such as Java, C++, Cobol, C, Pascal, Fortran, PL1, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and sub goals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

The invention and various specific aspects and embodiments will be better understood with reference to the following drawings and detailed descriptions. In some of the drawings and detailed descriptions below, the present invention is described in terms of the important independent embodiment of a system operating on a digital device or data network. This should not be taken to limit the invention, which, using the teachings provided herein, can be applied to other situations, such as cable television networks, wireless networks, etc. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

It is well known in the art that logic systems and methods such as described herein can include a variety of different components and different functions in a modular fashion.

Different embodiments of the invention can include different mixtures of elements and functions and may group various functions as parts of various elements. For purposes of clarity, the invention is described in terms of systems and/or methods that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Javascript, HTML, XML, dHTML, assembly or machine code programming, etc.

All references, publications, patents, and patent applications cited herein are hereby incorporated by reference in their entirety for all purposes. All documents, data, or other written or otherwise available material described or referred to herein, is herein to incorporated by reference. All materials in any IDS submitted with this application are hereby incorporated by reference.

When used herein, "the invention" should be understood to indicate one or more specific embodiments of the invention. Many variations according to the invention will be understood from the teachings herein to those of skill in the art.

BRIEF DESCRIPTIONS OF THE DRAWINGS

FIG. 1 illustrates an example of a portion of one type of data set that can be analyzed according to specific embodiments of the invention.

DESCRIPTION OF SPECIFIC EMBODIMENTS

1. Definitions

Figure 2:
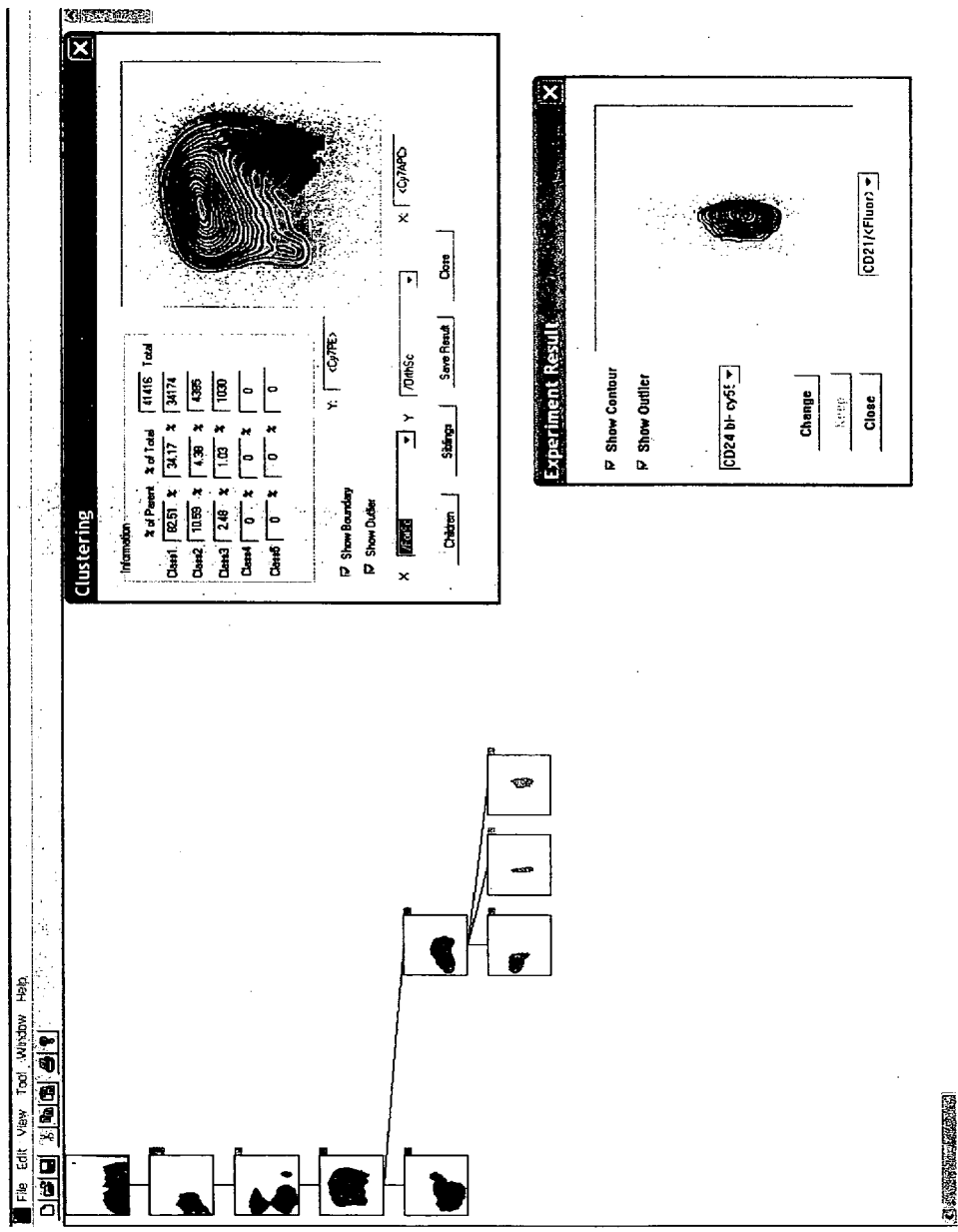
FIG. 2 illustrates an example user interface according to specific embodiments of the invention.

A "lattice" as used herein shall be understood to be a mathematically relationship relating to one or many dimensional analysis and representing a rules-based ordering of values used as a reference framework for performing analysis of various data-sets. Data analysis according to the present invention can be perform using reference values whether or not those values are described or describable as a lattice. For ease of illustration, a lattice herein may be drawn and discussed as comprising a two-dimensional, regular, finite and linear lattice. However, the present invention can be used with any system for determining coordinates in a data space, including lattices in three-dimensions, and higher dimensions, as well as non-linear regular lattices including logarithmic lattices, sinusoidal based lattices, etc., and rules-based lattices.

A "lattice point" as used herein shall be understood to indicate a data reduction point or region in any data space in which a lattice is defined. Thus a lattice point can have one, two, three, sixteen or any number of coordinates as appropriate for a dataspace. Placement of a lattice point can be accomplished a number of ways, including a geometric center in the number of coordinates of the dataspace, at predefined interstitial points on the lattice in a data space, etc.

2. Description of General Method

According to specific embodiments of the invention, a method of the invention can be understood within the art of data analysis, particularly statistical analysis and set analysis. The following description of general methods is presented in a particular order to facilitate understanding and it will be understood in the art that according to specific embodiments of the invention various steps can be performed in different orders and can be organized and/or atomized in different ways. A familiarity with the field of data set analysis and the reference mentioned herein will aid in understanding the invention.

Data Set

According to specific embodiments of the invention, a data set of observations is analyzed to determine meaningful clusters. For purposes of understand the invention, consider a large data set of n observations, where n can be very large, such as $n>>10^6$. FIG. 1 illustrates an example of a portion of one type of data set that can be analyzed according to specific embodiments of the invention. In a variety of different fields, each observation of interest will have associated with it a number of parameters where each parameter (or dimension) can represent some observed or calculated or predicted parameter relative to observation and/or sample $x_i$. For example, in FACS, a number of dimensions may be a light intensity measured for a particular cell and/or group and/or sample of cells, in market analysis each dimension may be a measure of different characteristics and/or predictions and/or observations related to a market participant $x_i$. In genetic analysis, parameters can be different states that a specific DNA/RNA location can represent. In protein analysis, each observation could be an amino acid and each parameter an angle or folding configuration or other state of the amino acid in a protein.

The Cluster Model

According to specific embodiments of the invention and as will be generally understood in the art, it is assumed that the observations can be clustered in at least two groups or clusters, with one of the at least two being a background state or cluster representing observations that are due to noise, etc. According to specific embodiments of the invention, the invention uses a method that can be employed on an information system to automatically determine a number of clusters that are useful and to assign data points and/or divide the data space to correspond to those clusters. The invention employs novel methods to do so even in large data set environments.

Data Reduction

Lattice/Grid

According to specific embodiments of the invention, a lattice or grid is determined in the data space according to a lattice rule. In generally terms, the lattice can be understood as simply a regular and normalized lattice in the number of dimensions and with normalization set to take account of a set of data points of interest. In a particular embodiment, the lattice has the same number of intervals in all directions. In this case, a lattice with M intervals in each direction will define $M^d$ lattice points.

Weighting

According to specific embodiments of the invention, each lattice point is assigned a weight that is based on one or more of the observed data points. Weights can be assigned in a number of fashions, but can be understood as the average of all the values in the data set near that point. The region of average for determining weights may be reduced.

Density Estimate

With the lattice points defined and each point having a set of weighted parameter values associated with it, the invention according to specific embodiments, next determines an estimated density surface that allows lattice points to be compared.

Determining Pointers/Paths Between Lattice Points

Using the lattice points, weights, and surface, the invention next traces out one or more paths between the lattice points. This analysis can be performed by beginning at any lattice point and making a directional connection to one of the surrounding lattice points following a rule based on the density surface, for example, a rule that seeks to follow the steepest path between points. Lattice points that do not have a surrounding point that meets the rule are terminal lattice points and are either associated with a new cluster or with a default background cluster. One or more methods can be used to split paths that converge on a false maximum.

According to specific embodiments of the invention, at the end of the analysis, each lattice point will have associated with it one or more directional pointers in one or more paths, with the paths defining one or more meaningful clusters.

In further specific embodiments, a lattice point either has one directed pointer emanating from it or not. The pointer from a first lattice point to a second lattice point represents an association between the first lattice point and the second lattice point. The lattice points may be scanned in any direction or manner to determine whether each of the particular lattice points possesses a pointer to any of the other neighboring lattice points. In specific embodiments, the determination of whether there is a pointer and to which lattice point the pointer points to is as follows and can be performed for every lattice point or for some subset of lattice points.

Example of Determining Existence of Direction of a Pointer

For a given lattice point, the value of the density estimate at that given lattice point may be compared to the value of the density estimate of all of the neighboring lattice points. If the former is smaller than the maximum of the latter, a pointer from the given lattice point is established to the neighboring lattice point where the maximum is attained. If the former is larger than the maximum of the later, then no pointer is created and that lattice point can be understood as representing a local maximum. After doing this at each lattice point, the result is one or more pointer chains, each consisting of a sequence of pointers that consecutively connect a number of lattice points. Several chains may end in the same lattice point.

According to specific embodiments of the invention, an example method can be described as choosing a lattice point and traversing the sequence of pointers emanating from that lattice point to a peak lattice point. If the density estimate of the last lattice point is above a certain threshold (such as the 65th percentile of all density estimates on the lattice), then this lattice point is labeled as the root of a cluster; if not, then all lattice points along the chain are labeled as background noise. Then the algorithm proceeds to the next chain. If the last lattice point of that chain was already traversed before, i.e. it is also a member of an earlier chain, then the chain is merged with the earlier chain, i.e. it points to the same root, or is assigned to background noise. Otherwise, this chain is dealt with as the first chain, resulting in a new root of a cluster or in an assignment to background noise. After the algorithm has dealt with all chains, each lattice point is assigned via a sequence of pointers to either a root of a cluster, or to background noise. Next, the algorithm determines whether some roots need to be merged.

Merging

If the distance of two roots is below a threshold (such as 3 lattice points), then they will be merged by giving them the same identifier. Two roots will also be merged if there is a path of consecutive lattice points along which the values of the density estimates (described in the previous paragraph) do not fall more than a certain amount below the minimum values of the two roots. For instance the minimum chosen may be 5% of the square root of the minimum value of the two roots. After each pair of roots has been considered, the algorithm iterates the procedure on the new roots until no more changes are made.

Thus, each resulting root represents a cluster. The cluster membership of each data point can be determined as follows. First one may find the nearest lattice point and then follow the chain of pointers to a root, which represents the cluster, or to a label assigning it to background noise. A list is established, which notes for each lattice point the pertaining cluster number, or notes that it is background noise.

For each cluster, all pertaining data points can be retrieved as follows: Going through the above list delivers all lattice points pertaining to that cluster, and the data points pertaining to each lattice point can be accessed e.g. via a Voronoi diagram.

Assigning Observed Points to Lattice Points

With the lattice points each assigned to a cluster or to background noise, the observations are assigned to clusters by relating each observation to a lattice point and then using the cluster assignment of the lattice point. This is accomplished by an assignment rule. One assignment rule that can be used according to specific embodiments of the invention is to assign each data point to the nearest (in Euclidean metric) lattice point, as described below.

3. Example User Interface

Figure 3:
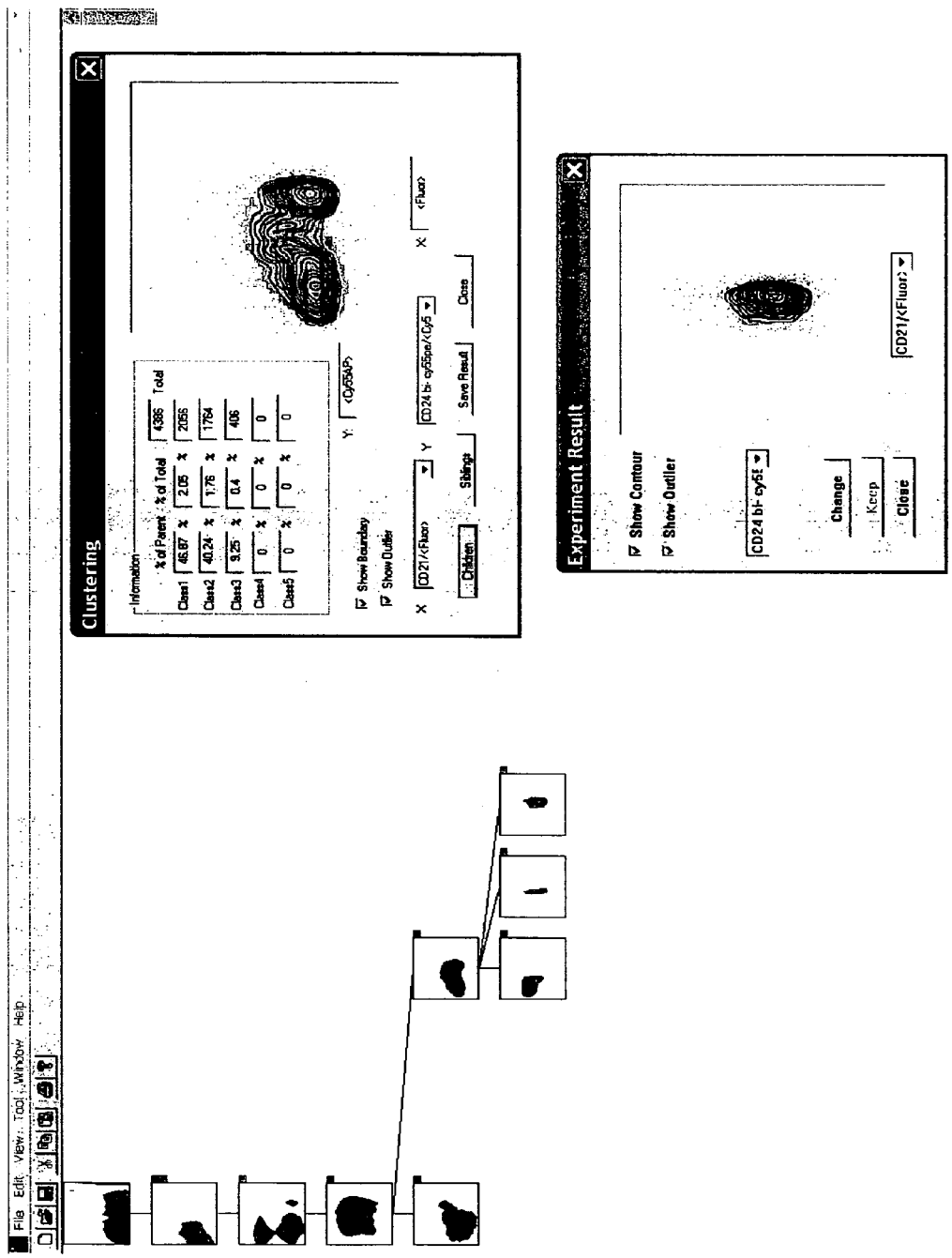
FIG. 3 illustrates an example user interface according to specific embodiments of the invention.

The algorithm may be executed through a web-page and web-server. An exemplary display will appear as shown in FIG. 2 or FIG. 3. An alternative embodiment may be the use of the present algorithm with a command line interface instead of a GUI interface.

Example Execution Environment

The preferred embodiment is for the present invention to be executed by a computer as software stored in a storage medium. The present invention may be executed as an application resident on the hard disk of a PC computer with an Intel Pentium or other microprocessor and displayed with a monitor. The processing device may also be a multiprocessor. The computer may be connected to a mouse or any other equivalent manipulation device. The computer may also be connected to a view screen or any other equivalent display device.

4. Example Detailed Description

The present invention can also be described using terms and mathematically notation that are generally familiar in the fields of statistical analysis. It would be a straightforward endeavor using the description provided below to configure and/or program an information processing system to perform in accordance with this mathematically description.

Data Set

Consider a data set of n observations $x_1, \ldots, x_n$, where n can be very large, such as $n \gg 10^6$ for example for FACS analysis or large scale population and/or market analysis. Each observation $x_i$ has d dimensions, where each dimension can represent some observed or calculated or predicted parameter relative to observation and/or sample $x_i$. For example, in FACS, a number of dimensions may be a light intensity measured for a particular cell and/or group and/or sample of cells, in market analysis each dimension may be a measure of different characteristics and/or predictions and/or observations related to a market participant $x_i$. In some FACS applications, for example, $d \approx 10$. Thus, in specific embodiments, each $x_i$ can be understood to denote an ordered set of values, representing the dimensions 1 to d, e.g., $x_i = \{d_1, d_2, d_3 \ldots, d_d\}$. or, using notation that will allow individual dimensions to be indicated for specific observations $x_i = \{x_{i,1}, x_{i,2}, x_{i,3} \ldots, x_{i,d}\}$.

In specific implementations, an implementation of the invention (e.g., a software implementation) according to specific embodiments uses d=2 and can, for example examine 2-dimensional projections and/or two-dimensional samples of higher-dimensional data. A method according to specific embodiments of the invention can further successively and/or selectively and/or interactively use various sets of 2 or more dimensions to perform clustering and can further select and/or combine results for different 2 or more dimensional analysis. The detailed interface example shows one example of an interactive two-dimensional analysis system allowing for successive analyses.

According to further specific embodiments of the invention, in selecting a cluster for further analysis, the invention may use extrinsic information either to enhance an interactive selecting or to perform an automatic selection of a cluster for further analysis. This intrinsic information can include information in a database, knowledge base or any other externally supplied information.

Furthermore, in the present discussion, assume that one or more dimensions/coordinates of observations $x_i$ are continuous for some given decimal precision.

For example, for FACS data, each observation $x_i$ could represents one cell and/or sample measured and each parameter and/or coordinate and/or dimensional value represents a measured characteristic of the cell. In many typical FACS systems, one or more parameters of an observed cell $x_i$ will represent a florescence color detected for a cell. As a further example, for marketing data, each observation $x_i$ can represent a market participant with each coordinate representing a certain characteristic and/or prediction and/or observation of the market participant such as income, confidence, buying characteristics, market power, etc.

The Cluster Model

According to specific embodiments of the invention and as will be generally understood in the art, it is assumed that the observations $x_1, \ldots, x_n$ are drawn from (or generated by) a density $$f(x) = \sum_{k=1}^{K} a_K g_k(x), a_K > 0, \sum_K a_K = 1. \tag{1}$$

where represent $g_k$ represent one of a number of clusters/components 1 through K and $a_k$ represents a percentage coefficient value that each cluster contributes to the total set of observed data. Thus, k represents a cluster index. In the art, it is sometimes said that the densities $g_k(x)$ are the component densities that represent the populations (or clusters).

Furthermore, according to specific embodiments of the invention from experience in the case of example FACS data, assume for the component densities $g_k$ that all level sets $L(t) = \{x \in R^d : g_k(x) \geq t\}$, $t \geq 0$, are path connected, that is for every $t \geq 0$ and every x, $y \in L(t)$ there exists a continuous function $p:[0,1] \to R^d$ such that $p(0)=x$, $p(1)=y$ and $p(u) \in L(t)$ for all $u \in [0,1]$.

Thus, according to the example model shown in Eq. (1), each observation $x_i$ arises from one of the components/clusters $g_k$, k=1, \ldots, K, where $g_1$ is a cluster that is understood or assigned to model 'background noise' (e.g., $g_1$ is understood as the source of all observations $x_i$ that are not related to, or grouped by any of the clusters $g_2, \ldots, g_K$).

An aspect of an example clustering procedure is to determine, based on $x_1, \ldots, x_n$, a value for K (e.g., how many components/clusters there are) and to determine a rule that assigns each observation $x_i$ and or each region of the relevant data space (to provide assignment for future observations not yet available) to one of the components/clusters $g_k$.

Example Data Reduction

Example Lattice/Grid Use

Again, typically $x_i$ can represent very large sets of data, include sets where the number of observations $x_i$ are much greater than $10^6$. Thus, to reduce the data set both to allow for easier computation and to provide other inferences, a data reduction technique using a lattice is used as described in detail below.

According to specific embodiments of the invention, a lattice L is constructed and/or assumed and/or defined in $R^d$ space consisting of $M^d$ points, where M is generally a positive integer, and for example for FACS applications can be such as 64 or 128. In general terms, such a lattice can be understood as simply a regular and normalized lattice in d dimensions where the normalization is set to take account of all or some subset of the observed data. Stated more formally, set $\Delta_j = \max_i x_{i,j} - \min_i x_{i,j})/(M-1)$, $j=1, \ldots, d$, in other words, set the size of a d-dimensional unit area or volume to be $\Delta_j$. Define the jth coordinate of lattice points $y_{(m1, \ldots, md)}$ to be $y_{mj} = \min_i x_{i,j} + (m_j - 1) \Delta_j$, $m_j = 1, \ldots, M$. Then the lattice L is defined as $L = \{y_{(m1, \ldots, md)} : (m_1, \ldots, m_d) \in \{1, \ldots, M\}^d\}$.

Example Weighting Assignment

Next, each lattice point $y_m$ is assigned a weight $w_m$ that, for example, is derived in part from one or more of the observed data points $x_i$ in the data space. One weight assignment example according to specific embodiments of the present invention is to use a linear binning technique such as:

$$w_m = \sum_{i=1}^{n} \prod_{j=1}^{d} \max(0, 1 - |x_{i,j} - y_{mj}|/\Delta_j).$$

While this particular example formally uses all of the observations $x_i$ in calculating each weighting faction, in fact points more than $\Delta_j$ away are largely not included in the weight for a particular $y_m$. Various other weighting functions, including functions that eliminate outlying points, etc., can be used to assign weights according to specific embodiments of the invention. Examples of such methods that can be employed according to specific embodiments of the invention are as described in Fan, hanging and Marron, James S. "Fast implementations of nonparametric curve estimators". Journal of Computational and Graphical Statistics. 1994, Vol. 3, 35-56.

Computing the Density Estimate

According to specific embodiments of the invention, at each lattice point $y_m$, a calculation is performed allowing the contours of the $y_m$ lattice points based on weights to be analyzed. One method for doing this is to compute an estimate of a density surface $\hat{f}(y_m)$. According to specific embodiments of the invention, this can be performed as follows. Denote the Gaussian kernel by $\phi(b) = 1/\sqrt{2\pi} \exp(-b^2/2)$. Then the estimated density at $y_m$ can be computed by:

$$\hat{f}(y_m) = 1/n \sum_{l_1=-Z_1}^{Z_1} \ldots \sum_{l_d=-Z_d}^{Z_d} w_{m-1} \prod_{j=1}^{d} \phi(l_j \Delta_j / h_j) / h_j,$$

where $l=(l_1, \ldots, l_d)$, $Z_j=\min(\lfloor 4h_j/\Delta_j \rfloor, M-1)$, and $h_j= SD(\{x_{i,j}, i=1, \ldots, n\}) n^{-1/(d+4)}$, where SD denotes standard deviation. The sum in the previous display can be computed quickly with the Fast Fourier Transform (FFT) in a well-known way, for example as discussed in Wand (1994), but it can also be computed directly using the above formula without the FFT. Note that while this expression has been written for clarity in terms of the observations $x_{i,j}$, it could equivalently be written in terms of $y_m$ and the weights.

Clustering by Associating Pointers Between Lattice Points

According to specific embodiments of the invention, clusters are determined in the lattice space defined by lattice points $y_m$ using a correlation between the lattice points, such as the density surface. In order to make associations between the lattice points, considering each lattice point $y_m$ in turn, according to specific embodiments, the invention computes $$\hat{\sigma}_m^2 = \frac{1}{n(n-1)} \sum_{l_1=-Z_1}^{Z_1} \ldots \sum_{l_d=-Z_d}^{Z_d} w_{m-1} \prod_{j=1}^{d} \phi^2(l_j \Delta_j / h_j) / h_j^2 - \frac{1}{n-1} \hat{f}(y_m)^2,$$

which can generally be understood as an estimate of the standard deviation of the density estimate. The sum can be computed with the FFT as above. Define the index set $S=\{m \in \{1, \ldots M\}^d : \hat{f}(y_m) > 4.3 * \sqrt{\hat{\sigma}_m^2}\}$.

According to specific embodiments of the invention, association pointers are used to determine clusters. These pointers can be understood as pointing from a lattice point to a neighboring lattice point. In specific embodiments, these pointers are established or removed by successively executing a series of evaluations, such as described below.

Step 1:

For all lattice points $y_m$, where $m \in S$, in turn:

Consider all the neighboring lattice points $p_1, \ldots, p_{n\ m}$ which are defined as the set of all lattice points contained in a d-dimensional rectangular volume. Let $p \in \{p_1, \ldots, p_{n\ m}\}$ such that $\hat{f}(p) = \max_{k=1,\ldots,n\ m} \hat{f}(p_k)$, splitting ties in an arbitrary manner. Then step 1 establishes an association pointer from $y_m$ top provided the following two conditions hold:

$$\hat{f}(p) > \hat{f}(y_m); \text{ and}$$

$$\frac{\partial}{\partial e} \hat{f}(y_m) > \lambda_m,$$

where $e=(p-y_m)/\|p-y_m\|$, $\|\cdot\|$ denotes Euclidean norm, and $$\frac{\partial}{\partial e} \hat{f}(y_m) = \sum_{a=1}^{d} e \frac{\partial}{\partial y_{m_a}} \hat{f}(y_m),$$

which indicates a gradient of the density estimate, $$\frac{\partial}{\partial y_{m_a}} \hat{f}(y_m) = 1/n \sum_{l_1=-Z_1}^{Z_1} \ldots \sum_{l_d=-Z_d}^{Z_d} w_{m-1} \frac{-l_a \Delta_a}{h_a^2} \prod_{j=1}^{d} \phi(l_j \Delta_j / h_j) / h_j$$

$$\lambda_m = q(0.95^{1/\kappa}) \sqrt{\Sigma_m^2}$$

$$\kappa = \frac{\#S \sum_{m \in s} w_m}{n(2\pi)^{d/2} \prod_{j=1}^{d} h_j \sum_{m \in s} w_m \hat{f}(y_m)}$$

$$\hat{\Sigma}_m^2 = \frac{1}{n-1} \left( \sum_{a,b=1}^{d} e_a e_b \left[ A - \frac{\partial}{\partial y_{m_a}} \hat{f}(y_m) \frac{\partial}{\partial y_{m_b}} \hat{f}(y_m) \right] \right)$$

$$A = 1/n \sum_{l_1=-Z_1}^{Z_1} \ldots \sum_{l_d=-Z_d}^{Z_d} w_{m-1} \frac{l_a l_b \Delta_a \Delta_b}{h_a^2 h_b^2} \prod_{\varphi=1}^{\delta} \phi^2(l_j \Delta_j / h_j) / h_j^2$$

(A is an estimate of $$\left( A \text{ is an estimate of } \frac{\partial}{\partial y_{m_a}} f(y_m) \frac{\partial}{\partial y_{m_b}} f(y_m) \cdot \right)$$

denotes the 100·xth percentile of the standard normal distribution. All the sums can be computed with the FFT as above.

Step 2:

From each lattice point $y_m$, $m \notin S$, a pointer is established that points to a state representing the background noise.

Step 3:

For all lattice points $y_m$, $m \in S$, in turn:

If a pointer originates at $y_m$, then it will point to a different lattice point, which itself may have a pointer originating from it. A succession of pointers is followed until one arrives at a lattice point $y_z$ is reached that either (a) does not have any pointer originating from it, or (b) has a pointer originating from it that points to a state representing a cluster or background noise.

In case (a), all the pointers visited in the succession will be removed and new pointers originating from each lattice point visited in the succession will be established to the background noise state, provided that: $\hat{f}(y_z) < q(0.95^{1/\kappa}) \sqrt{\hat{\sigma}_z^2}$. Otherwise, only the pointer originating from $y_z$ (if any) will be removed, and a new pointer will be established that originates from $y_z$ and points to a newly cluster state. In case (b) above, no pointers are removed or established.

Step 4:

Let $\{y_{m(1)}, \ldots, y_{m(k)}\}$ be the set of all lattice points which have a pointer originating from them to a dummy state representing a cluster, enumerated such that $\hat{f}(y_{m(1)}) \geq \ldots \geq \hat{f}(y_{m(k)})$, and for $i=1, \ldots, k$ do:

Set $A=\{m(i)\}$. Iterate the following loop until no more indices are added to A:

(Begin loop)

For each index $a \in A$ in turn, add all the indices p to A that satisfy:

$y_p$ is a neighbor or $y_a$ as defined in step 1, and no pointer originates from $y_p$, and $$\hat{f}(y_p) + \hat{\sigma}_p \geq \hat{f}(y_{m(i)}) + \hat{\sigma}_{m(i)}$$

(End loop)

Denote by B the set of indices of lattice points from which a pointer originates to a cluster state and that also have some $y_p$, $p \in$ as neighbor. If B is not empty, then do the following:

Define q by $\hat{f}(y_q) = \max_{r \in B} \hat{f}(y_r)$, breaking ties arbitrarily.

Establish a pointer from each $y_p$, $p \in A \setminus \{m(i)\}$, to $y_q$

For each $r \in B$, $r \neq q$: remove the pointer from $y_r$ to the state representing a cluster, and establish a new pointer from $y_r$ to $y_q$.

(End Loop Over i)

Step 5:

Repeat step 4 until there are no more additions or deletions of pointers to cluster state.

Step 6:

From each lattice point that does not have pointer originating from it, establish a pointer pointing to the background noise state.

Lattice Point Results

With the above described procedure, according to specific embodiments of the invention, every lattice point has a pointer originating from it. Following the succession of pointers leads to a state outside of the lattice point space which either represents a background noise or a cluster. All lattice points that are linked pertain to the same cluster or to background noise.

Assigning Observed Points to Lattice Points

With the lattice points each assigned to a cluster or to background noise, observations $x_i$ are assigned to clusters by relating each observation to a lattice point and then using the cluster assignment of the lattice point. This is accomplished by an assignment rule. In specific embodiments, each observation $x_i$ is assigned to the lattice point $y_m$ that is closest to $x_i$ in Euclidean norm. Then $x_i$ is assigned to the same cluster to which its associated lattice point $y_m$ is assigned. Likewise, all observations assigned to a certain cluster can be found as follows: Find all lattice points $y_m$ that the algorithm assigns to the given cluster, then find all observations $x_i$ that are assigned to these lattice points.

5. Example Interface

FIG. 2 illustrates an example user interface according to specific embodiments of the invention. FIG. 3 illustrates an example user interface according to specific embodiments of the invention. From the left is illustrated a tree that shows parent-children relationships of clustering results.

In the upper right window is illustrated detailed information regarding three identified clusters (Class1, Class2, and Class3) at a particular iteration of the cluster selection. The details shown in this example interface include, for each cluster/class, the % of the selected parent cluster that is in this identified cluster (e.g., 82.51 for Class1), the % of the total population that is in this identified cluster (e.g., 34.17 for Class 1), and the total number of observations in that class (e.g., 34174). In this example, the total number of observations being analyzed in these displayed clusters is as indicated in the figure. (e.g., 41416).

According to specific embodiments of the invention, an interface such as that shown can also include labels indicating X and Y parameters, option inputs to show boundaries and/or contours and/or outliers, and inputs to save results.

From this window, clustering of other regions can be performed by selecting children to indicate a sub region or siblings to indicate a different clustering to be performed from the parent and further inputting the desired clustering parameters using the drop down X and Y inputs shown. FIG. 3, for example, shows a three children clusters identified from class 2 of FIG. 1.

According to specific embodiments of the invention, the right-bottom window is a window to allow a user to try different clustering parameters. The results in this window are not kept until a user chooses to do this by clicking the "keep" button.

Thus, according to specific embodiments of the invention, the invention automatically finds clusterings for a user that they must find manually otherwise. The interface provides a clear and hierarchical display to indicate the clusterings results.

6. Embodiment in a Programmed Information Appliance

Figure 4:
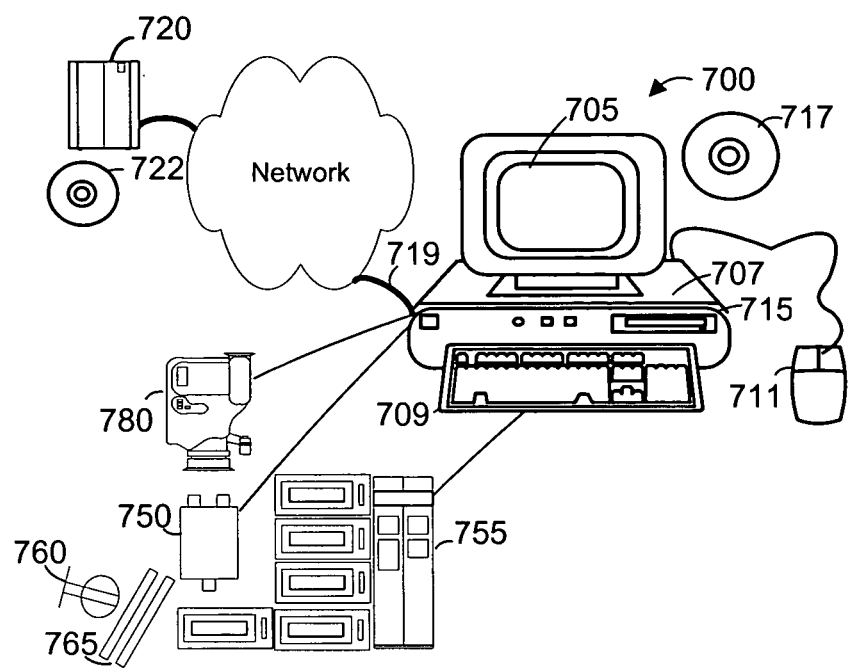
FIG. 4 is a block diagram showing a representative example logic device in which various aspects of the present invention may be embodied.

FIG. 4 is a block diagram showing a representative example logic device in which various aspects of the present invention may be embodied. As will be understood from the teachings provided herein, the invention can be implemented in hardware and/or software. In some embodiments, different aspects of the invention can be implemented in either client-side logic or server-side logic. Moreover, the invention or components thereof may be embodied in a fixed media program component containing logic instructions and/or data that when loaded into an appropriately configured computing device cause that device to perform according to the invention. A fixed media containing logic instructions may be delivered to a viewer on a fixed media for physically loading into a viewer's computer or a fixed media containing logic instructions may reside on a remote server that a viewer accesses through a communication medium in order to download a program component.

FIG. 4 shows an information appliance or digital device 700 that may be understood as a logical apparatus that can perform logical operations regarding image display and/or analysis as described herein. Such a device can be embodied as a general purpose computer system or workstation running logical instructions to perform according to specific embodiments of the present invention. Such a device can also be custom and/or specialized laboratory or scientific hardware that integrates logic processing into a machine for performing various sample handling operations. In general, the logic processing components of a device according to specific embodiments of the present invention is able to read instructions from media 717 and/or network port 719, which can optionally be connected to server 720 having fixed media 722. Apparatus 700 can thereafter use those instructions to direct actions or perform analysis as understood in the art and described herein. One type of logical apparatus that may embody the invention is a computer system as illustrated in 700, containing CPU 707, optional input devices 709 and 711, storage media (such as disk drives) 715 and optional monitor 705. Fixed media 717, or fixed media 722 over port 719, may be used to program such a system and may represent a disk-type optical or magnetic media, magnetic tape, solid state dynamic or static memory, etc. The invention may also be embodied in whole or in part as software recorded on this fixed media. Communication port 719 may also be used to initially receive instructions that are used to program such a system and may represent any type of communication connection.

FIG. 4 shows additional components that can be part of a diagnostic system in some embodiments. These components include a microscope or viewer or detector 750, sampling handling 755, light source 760 and filters 765, and a CCD camera or capture device 780 for capturing digital images for analysis as described herein for luminance detection. It will be understood to those of skill in the art that these additional components can be components of a single system that includes logic analysis and/or control. These devices also may be essentially stand-alone devices that are in digital communication with an information appliance such as 700 via a network, bus, wireless communication, etc., as will be understood in the art. It will be understood that components of such a system can have any convenient physical configuration and/or appear and can all be combined into a single integrated system. Thus, the individual components shown in FIG. 4 represent just one example system.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

7. Other Embodiments

The invention has now been described with reference to specific embodiments.

Other embodiments will be apparent to those of skill in the art. In particular, a viewer digital information appliance has generally been illustrated as a personal computer. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed:

1. A computer-implemented method for identifying clusters of observed data items in a data space comprising:
   a) defining an N-dimensional normalized lattice comprising a plurality of lattice points used as data reduction points in a data space of said data items, wherein said lattice points have a regular placement and distance relationship to each other;
   b) obtaining a set of n observed data items and parameter values from an information system, wherein the parameter values are associated with the observed data items;
   c) reducing the observed data items to lattice points and lattice point weights by performing steps of: identifying one or more data items within a predetermined distance of each lattice point, and calculating lattice point weights by applying a weighting rule that averages the parameter values associated with the observed data items within a predetermined distance of each lattice point;
   d) determining paths between lattice points by performing steps of: defining an estimated density surface for comparing lattice points within a predetermined distance, and creating directional associations between lattice points and at least one other lattice point within a predetermined distance by applying an association rule based on said estimated density surface;
   e) determining a lattice point path by performing steps of: sequentially connecting, based on said directional associations, a first lattice point and one or more subsequent lattice points within a predetermined distance until a terminal lattice point is reached, wherein said terminal lattice point is not connectable to any other lattice point based on said association rule;
   f) assigning lattice points in the data space to clusters or background noise by performing steps of: comparing the terminal lattice points of a said lattice point paths to a density threshold and defining the terminal lattice point as belonging to a new cluster, an existing cluster, or background noise; labeling the lattice points in lattice point path as points belonging to said new cluster, existing cluster, or background points based on said comparing; repeating said comparing and labeling steps until the remaining lattice points are labeled as belonging to a previously identified cluster or to background noise;
   g) distance merging clusters of lattice points in the data space by performing steps of: associating each cluster of lattice points with a root indicating the maximum terminal lattice point for that cluster; determining distances between roots, and merging clusters associated with said roots if the distance between the roots is below a distance threshold;
   h) density merging roots of clusters of lattice points in the data space by performing steps of: examining the roots of clusters, determining paths along consecutive lattice points to other roots, and merging roots of clusters when the path of consecutive lattice points densities falls below a minimum density threshold; repeating said density merging until no pairs of roots meet a density merging criteria;
   i) assigning the observed data items to clusters of lattice points in the data space by performing steps of: applying an assignment rule that assigns each observed data item to the closest lattice point within a predetermined distance; and assigning each observed data item to the same cluster to which its associated lattice point is assigned; and
   j) displaying the clusters of observed data items to a user graphical format, wherein steps a) through j) are performed on a suitably programmed computer.

2. The method of claim 1, wherein said set of n observed data items represents a set of one or more fluorescence levels obtained from a particular fluorescence channel of a fluorescence-activated cell sorter (FACS); and wherein said clusters of observed data items each provide an indication of separable cell subpopulations analyzed by said cell sorter.

3. The method of claim 1, wherein said data space has N dimensions and each N corresponds to a number of values of interest associated with at least one of said data items; and wherein said regular placement and distance relationship of lattice points is determined by a lattice rule that examines smallest and largest values of interest in each dimension and determines the lattice spacing.

4. The method of claim 3, wherein said lattice spacing is determined according to a spacing rule comprising taking the difference between smallest and largest values of interest in each dimension and defining a regular spacing of M units, where M represents a desired granularity.

5. The method of claim 1 wherein said association rule comprises:

determining density values of a plurality of lattice points by:
  using a kernel density estimate of weights on a lattice point to determine a density estimate at each of said plurality of lattice points; and
  at a lattice point, determining for a plurality of surrounding lattice points whether to make a directional association.

6. The method of claim 1 wherein said association rule comprises:
  determining a density surface for said lattice points;
  making a directional association if a slope of said density surface from a first lattice point to a second lattice point is significantly positive.

7. The method of claim 1, wherein said creating directional associations further comprises breaking spurious path terminations prior to said assigning lattice points in the data space to clusters or background noise.

* * * * *